United States Patent [19]

Tomita et al.

[11] 4,393,056
[45] Jul. 12, 1983

[54] ANTIBIOTICS TETRONOLIDE COMPOUNDS AND PROCESS FOR PRODUCTION THEREOF

[75] Inventors: Fusao Tomita; Tatsuya Tamaoki; Kunikatsu Shirahata, all of Machida; Masaji Kasai, Fujisawa; Noriaki Hirayama, Machida; Makoto Morimoto, Numazu, all of Japan; Masanori Fukui, Chicago, Ill.

[73] Assignee: Kyowa Hakko Kogyo Co., Ltd., Tokyo, Japan

[21] Appl. No.: 273,377

[22] Filed: Jun. 15, 1981

[30] Foreign Application Priority Data

Jun. 14, 1980 [JP] Japan ................................. 55-80482

[51] Int. Cl.³ .................. A61K 31/71; C07G 11/00
[52] U.S. Cl. .................................... 424/181; 536/7.1; 536/16.8; 549/265; 549/268
[58] Field of Search .............. 260/343.3 R; 536/17 R; 424/181; 549/265, 268

[56] References Cited

U.S. PATENT DOCUMENTS

| | | | |
|---|---|---|---|
| 3,144,466 | 8/1964 | Celmer ................................. | 549/265 |
| 3,903,072 | 9/1975 | Ilavsky et al. ...................... | 424/181 |
| 4,161,523 | 7/1979 | Weinstein et al. .................. | 424/181 |
| 4,346,075 | 8/1982 | Tomita et al. ...................... | 536/16.8 |

OTHER PUBLICATIONS

J. of Antibiotics, vol. 33, No. 6, pp. 668-670, Jun. 1980, "Novel Antitumor Antibiotics, Tetrocarcins", F. Tomita, et al.

J. of Antibiotics, vol. 33, No. 9, pp. 940-945, Sep. 1980, "Tetrocarcins, Novel Antitumor Antibiotics", F. Tomita, et al.

J. of Antibiotics, vol. 33, No. 9, pp. 946-950, Sep. 1980, "Tetrocarcins, Novel Antitumor Antibiotics", T. Tamaoki, et al.

Tetrahedron Letters, vol. 21, pp. 2559-2560, 1980, "The Structure of Tetronolide . . . ", Hirama, et al.

23rd Symposium Papers, pp. 584-591, Oct. 1980, (The Chemistry of Natural Product).

J. Antibiotics, vol. 33, 244-246, Feb. 1980, "A New Antibiotic, Antlermicin A", Kobinta, et al.

Primary Examiner—Ethel G. Love
Attorney, Agent, or Firm—Fitzpatrick, Cella, Harper & Scinto

[57] ABSTRACT

New antibacterial tetronolide compounds F-1 and F-2 are produced by fermentation of a microorganism belonging to the genus Micromonospora. The antibiotics F-1 and F-2 are accumulated in the culture liquor and are isolated therefrom respectively and the acyl derivatives of F-1 and F-2, that is, F-1-21-O-acetate, F-1-21-O-propionate, F-1-21-O-n-butylate, F-1 diacetate, F-1 dipropionate, F-2 triacetate, F-2 tripropionate and F-2 tri-n-butylate, etc., are synthesized from F-1 and F-2 by known means.

2 Claims, 8 Drawing Figures

ANTIBIOTICS TETRONOLIDE COMPOUNDS AND PROCESS FOR PRODUCTION THEREOF

RELATED APPLICATIONS

The present invention is related generally to the invention disclosed in U.S. patent application Ser. No. 31,912 filed on Apr. 20, 1979, now abandoned and its continuation in part Application Ser. No. 252,062 filed on Apr. 8, 1981, now U.S. Pat. No. 4,346,075, claiming antibiotic DC-11 and process for production thereof.

BACKGROUND OF THE INVENTION

The present invention relates to new compositions of matter having antibacterial and anti-tumor activities, such compositions of matter being designated as tetronolide compounds. The invention also pertains to the production of tetronolide compounds F-1 and F-2 by culturing a microorganism belonging to the genus Micromonospora which is capable of producing F-1 and/or F-2, in a nutrient medium until antibacterial activity is detected in the culture liquor and then recovering F-1 and/or F-2 and pertains to the production of the acyl derivatives of F-1 and F-2 by conventional methods.

Compounds which have antibacterial or anti-tumor activity are always in demand. To this end, it has been found that when a certain strain of Micromonospora is cultured in a nutrient medium, novel antibiotics tetrocarcins are produced in the culture liquor. The chemical, physical and biological properties of tetrocarcins isolated from the culture liquor and the process for the production thereof are described in Journal of Antibiotics 33, No. 6, P. 668 (1980), ibid. 33, No. 9, P. 940 and ibid. 33, No. 9, P.946.

Further, the chemical, physical and biological properties of DC-11 (tetrocarcin A) and the process for the production thereof is explained in detail in the specifications of the aforementioned U.S. patent application and its continuation in part application.

It has now been found that *Micromonospora chalcea* KY 11091, NRRL 11289, when cultured liberates two further active substances, namely F-1 and F-2 and the active derivatives of F-1 and F-2 are produced by conventional method using F-1 and/or F-2 as a starting material. A study of the chemical, physical and biological properties of these active substances indicates that the compositions of matter are new compounds which have now been named tetronolide (F-2), 17-O-tetronitrosyl-tetronolide (F-1), etc.

SUMMARY OF THE INVENTION

In accordance with the present invention, novel compounds, tetronolide (F-2) and 17-O-tetronitrosyl-tetronolide (F-1) are produced by fermentation of a microorganism belonging to the genus Micromonospora which is capable of producing F-1 and/or F-2 in a nutrient medium. At the completion of culturing, F-1 and/or F-2 are isolated from the culture liquor by known means such as silica gel chromatography.

The acyl derivatives of F-1 and F-2, such as F-1-21-O-acetate, F-1-21-O-propionate, F-1-21-O-n-butylate, F-1 diacetate, F-1 dipropionate, F-1 dibutylate, F-2 triacetate, F-2 tripropionate and F-2 tri-n-butylate, are produced by known means using F-1 and/or F-2 as a starting material. Those tetronolide compounds exhibit antibacterial activity and are useful to clean and sterilize laboratory glassware and surgical instruments and may also be used in combination with soaps, detergents and wash solutions for sanitary purpose. The compounds are also expected to be useful in the treatment of bacterial infections in animals due to its antibacterial properties. Moreover, as will be clear from the following description, tetronolide compounds may also be useful as an anti-tumor agent in animals.

BRIEF DESCRIPTION OF DRAWINGS

FIG. 8 shows the PMR spectrum of F-2 triacetate.

Figure 4:
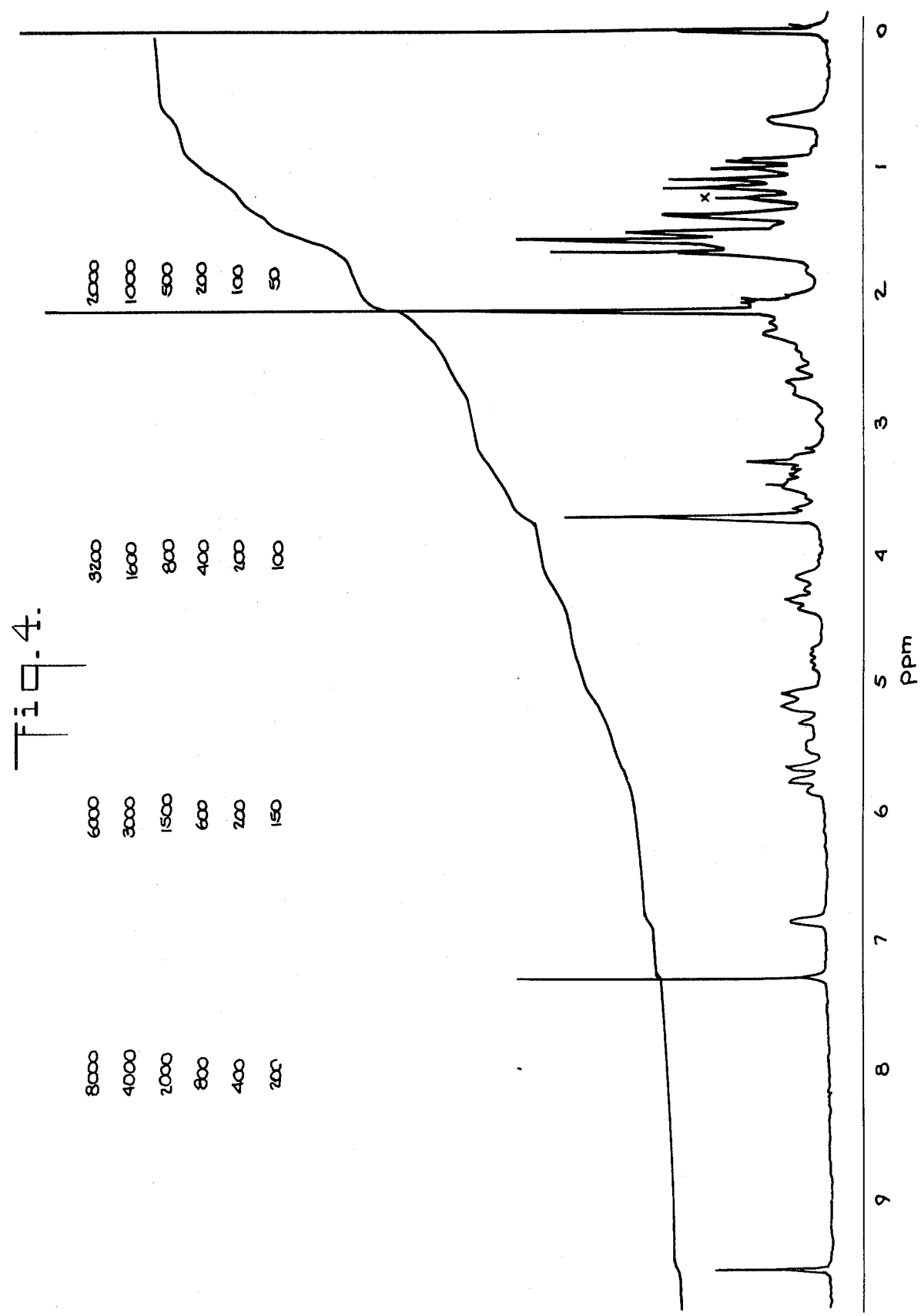
FIG. 4 shows the PMR spectrum of F-1 diacetate.
Figure 6:
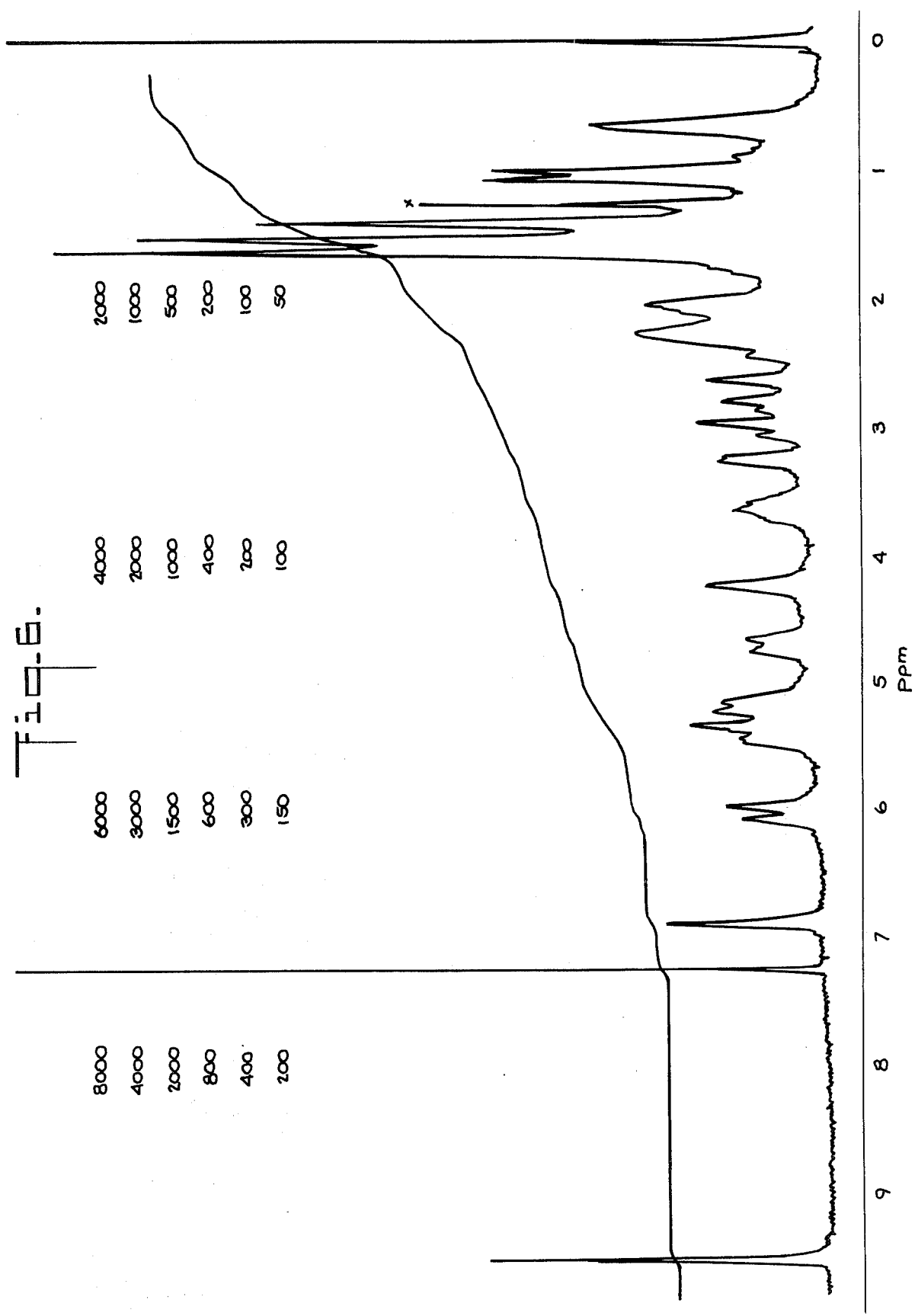
FIG. 6 shows the PMR spectrum of F-2.

The peaks represented by the mark "X" in FIG. 4, FIG. 6 and FIG. 8 are attributed to impurities.

DESCRIPTION OF THE INVENTION

Tetronolide compounds represented by the formula (1)

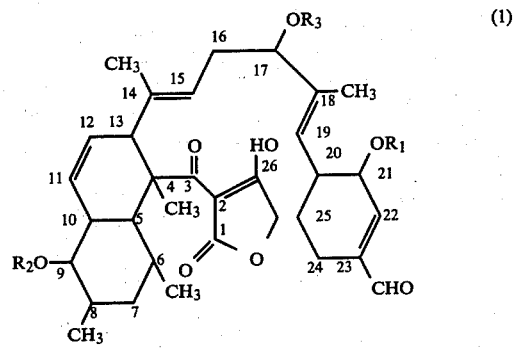

wherein $R_1$ and $R_2$ may be the same or different substituents and represent a hydrogen atom or an acyl group and $R_3$ represents a hydrogen atom, an acyl group or a tetronitrose represented by the formula (2)

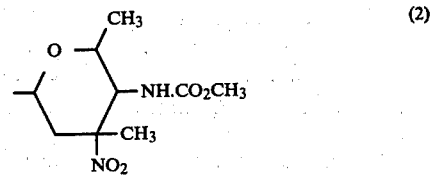

are novel compositions of matter having antibacterial and anti-tumor activities. The physicochemical properites of tetronolide compounds presented by the present invention are as follows.

(1) 17-O-tetronitrosyl tetronolide (Compound F-1)

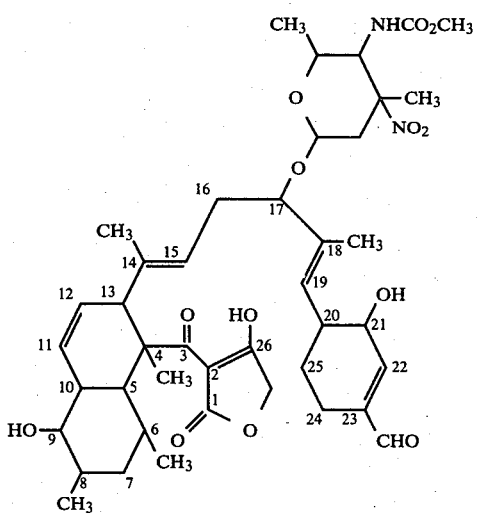

(1) Melting point: 207°–210° C.

| (2) Elementary analysis: | C (%) | H (%) | N (%) |
|---|---|---|---|
| Calculated | 62.90 | 6.95 | 3.58 |
| Found | 62.90 | 7.16 | 3.65 |

Figure 1:
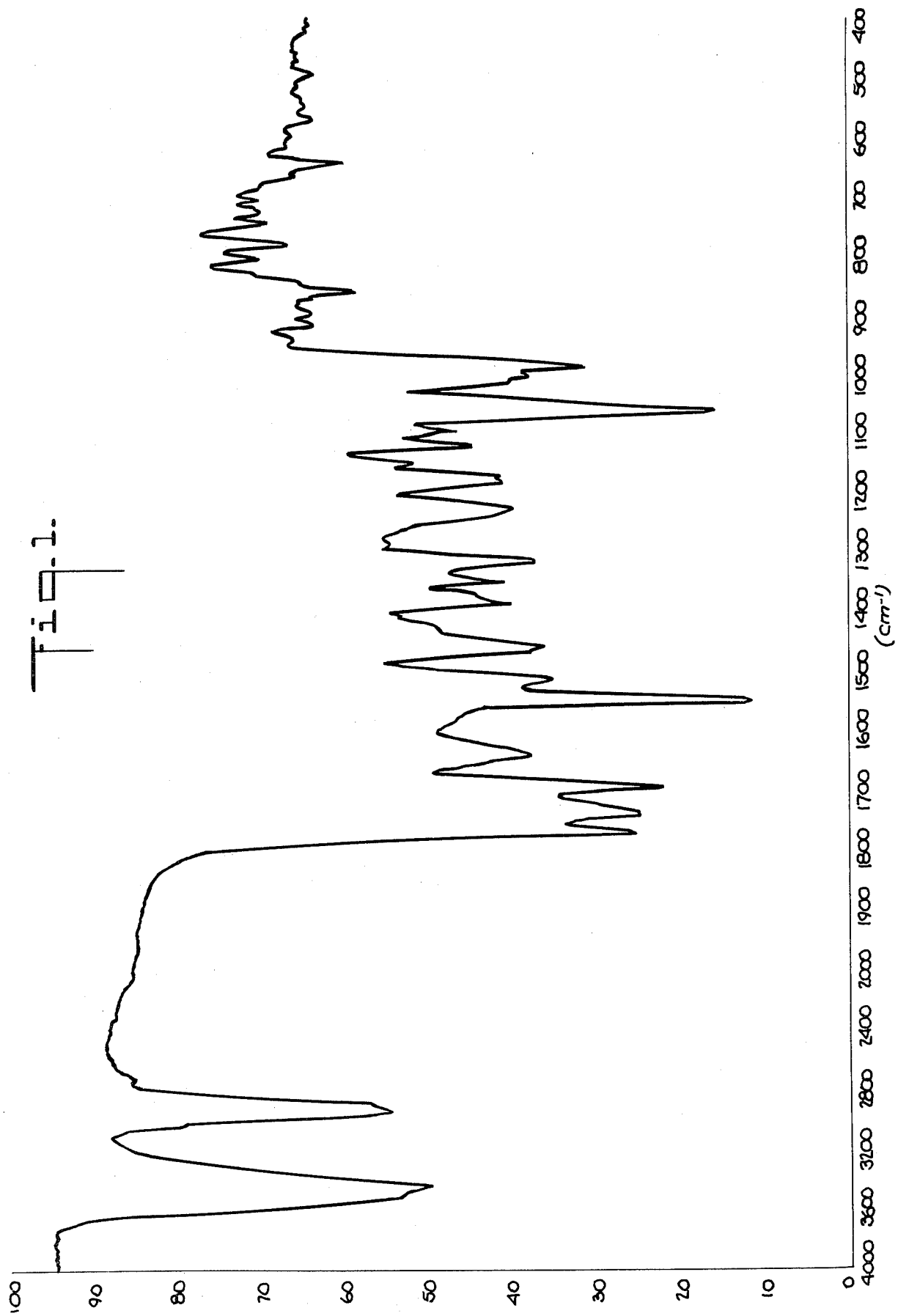
FIG. 1 shows the infrared absorption spectrum of 17-O-tetronitrosyl-tetronolide (F-1).

(3) IR spectrum (KBr tablet method): FIG. 1

Figure 2:
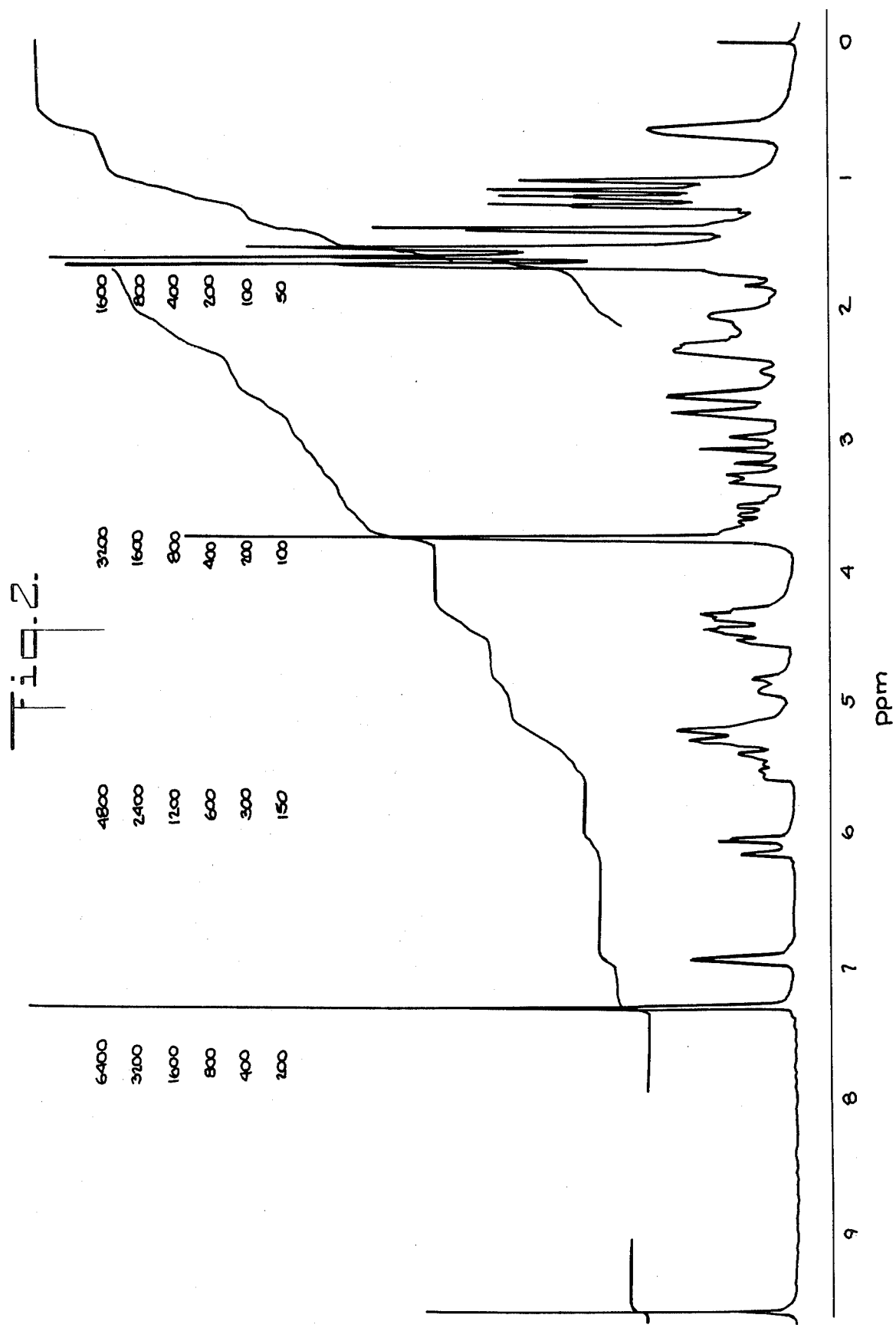
FIG. 2 shows the PMR spectrum of F-1.

(4) PMR spectrum (in CDCl$_3$, internal standard: TMS): FIG. 2)

(5) CMR spectrum (in CDCl$_3$, internal standard: TMS): 206.5, 201.5, 192.5, 166.5, 157.4, 149.6, 141.1, 136.2(two peaks), 126.3, 125.8, 123.0, 118.4, 100.9, 96.4, 91.7, 83.9, 77.9, 75.8, 69.4(two peaks), 54.4, 53.7, 52.7, 51.3, 44.8, 42.9, 41.7, 39.2, 35.9, 34.8, 31.0(two peaks), 29.7, 25.3, 22.1, 16.9, 16.1, 15.1, 14.3, 13.0 (ppm)

(2) Tetronolide (Compound F-2)

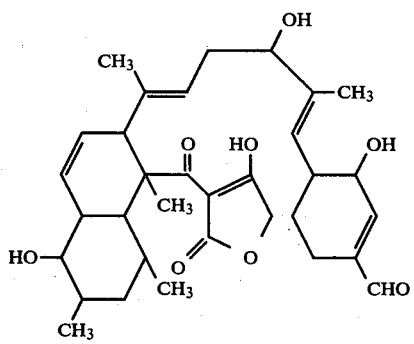

(1) Melting point: 211°–213° C.

| (2) Elementary analysis: | C (%) | H (%) |
|---|---|---|
| Calculated | 69.54 | 7.30 |
| Found | 69.26 | 7.51 |

Figure 3:
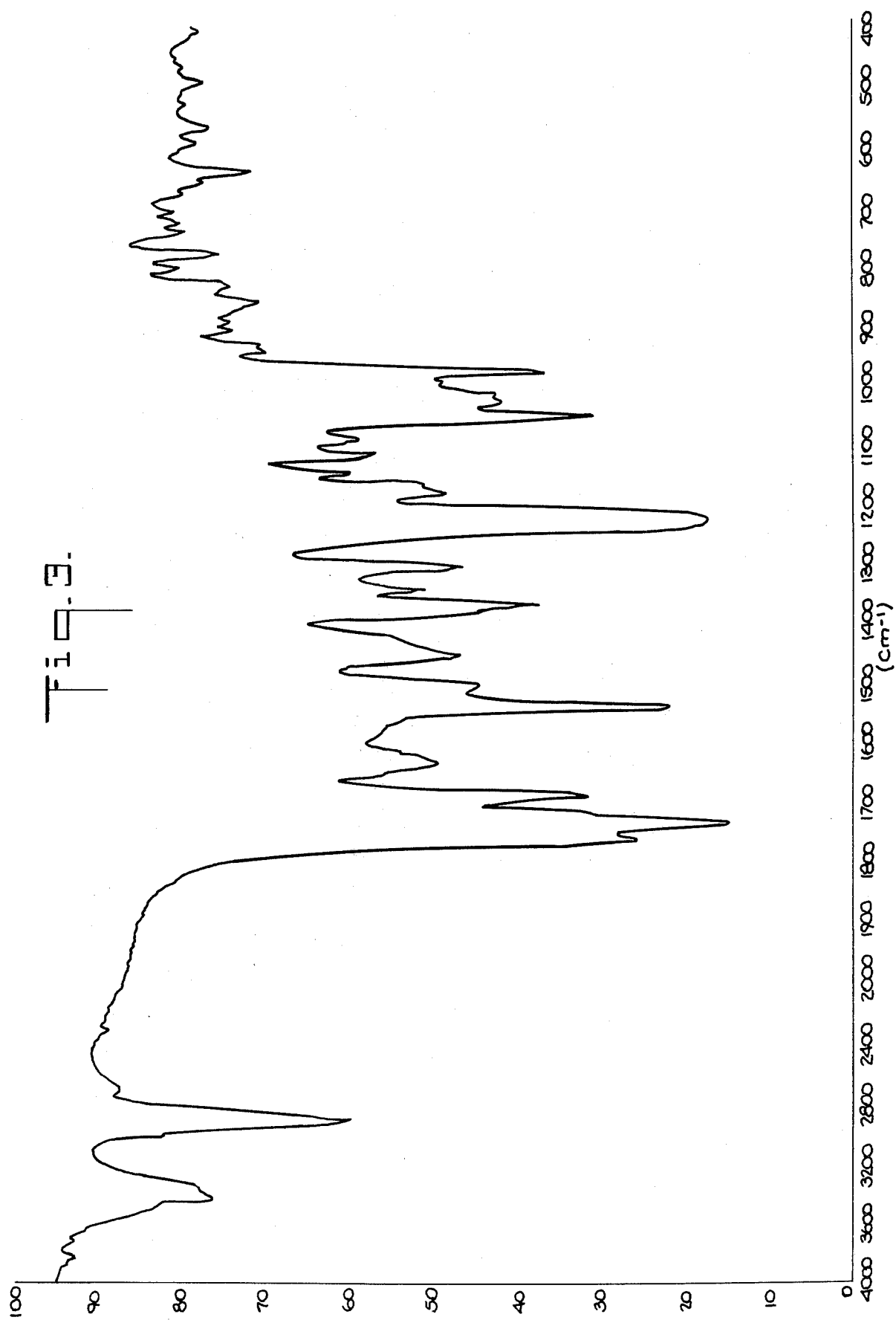
FIG. 3 shows the infrared absorption spectrum of 9,21-O-diacetyl-17-O-tetronitrosyltetronolide (F-1 diacetate).

(3) IR spectrum: FIG. 3

(4) PMR spectrum (in CDCl$_3$, internal standard: TMS): FIG. 4

(5) CMR spectrum (in CDCl$_3$, internal standard: TMS): 206.4, 201.3, 192.5, 167.2, 149.7, 144.5, 136.4, 136.1, 126.1, 125.9, 122.8, 117.2, 100.9, 84.1, 75.8, 72.8, 69.3, 54.3, 51.2, 45.2, 42.9, 41.6, 39.2, 34.7, 31.9, 31.1, 29.7, 22.1, 15.8, 15.1, 14.3, 13.0

(3) 21-O-Acetyl-17-O-tetronitrosyl tetronolide (referred to as "Compound F-1 monoacetate")

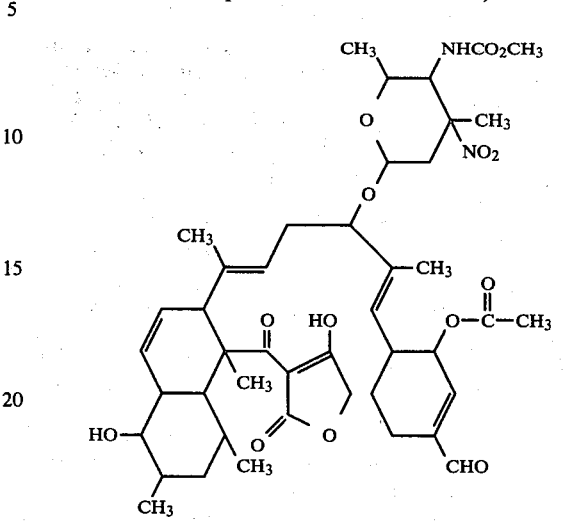

| (1) Elementary analysis: | C (%) | H (%) | N (%) |
|---|---|---|---|
| Calculated | 62.61 | 6.84 | 3.40 |
| Found | 62.73 | 7.00 | 3.39 |

(2) PMR spectrum (in CDCl$_3$, internal standard: TMS): 9.56(s), 6.87(s), 6.1–4.2 (many peaks are observed), 3.72(s), 3.7–2.2 (many peaks are observed), 2.12(s), 1.66(s), 1.58(s), 1.52(s), 1.40(s), 1.15(d), 1.05(d), 0.65(bs)

(3) CMR spectrum (in CDCl$_3$, internal standard: TMS): 206.5, 201.3, 192.1, 170.3, 166.2, 157.3, 145.3, 141.4, 137.2, 135.9, 126.1, 125.8, 123.4, 117.4, 100.8, 97.7, 90.7, 83.8, 78.6, 75.8, 71.8, 68.6, 54.3, 53.8, 52.8, 51.3, 42.9, 41.9, 41.6, 39.3, 35.9, 34.8, 31.4, 31.1, 30.0, 25.2, 22.0, 20.9, 17.1, 16.0, 15.1, 14.4, 13.0

(4) 9,21-O-Diacetyl-17-O-tetronitrosyl tetronolide (referred to as "Compound F-1 diacetate", hereinafter)

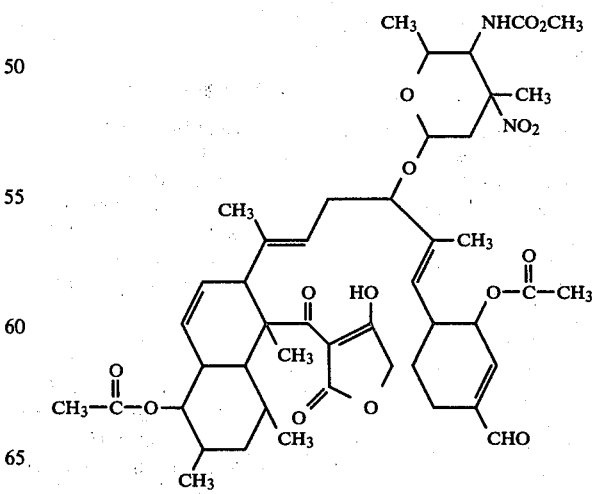

(1) Melting point: 193°–195° C.

| (2) Elementary analysis: | C (%) | H (%) | N (%) |
|---|---|---|---|
| Calculated | 62.34 | 6.74 | 3.23 |
| Found | 61.96 | 6.95 | 3.04 |

Figure 5:
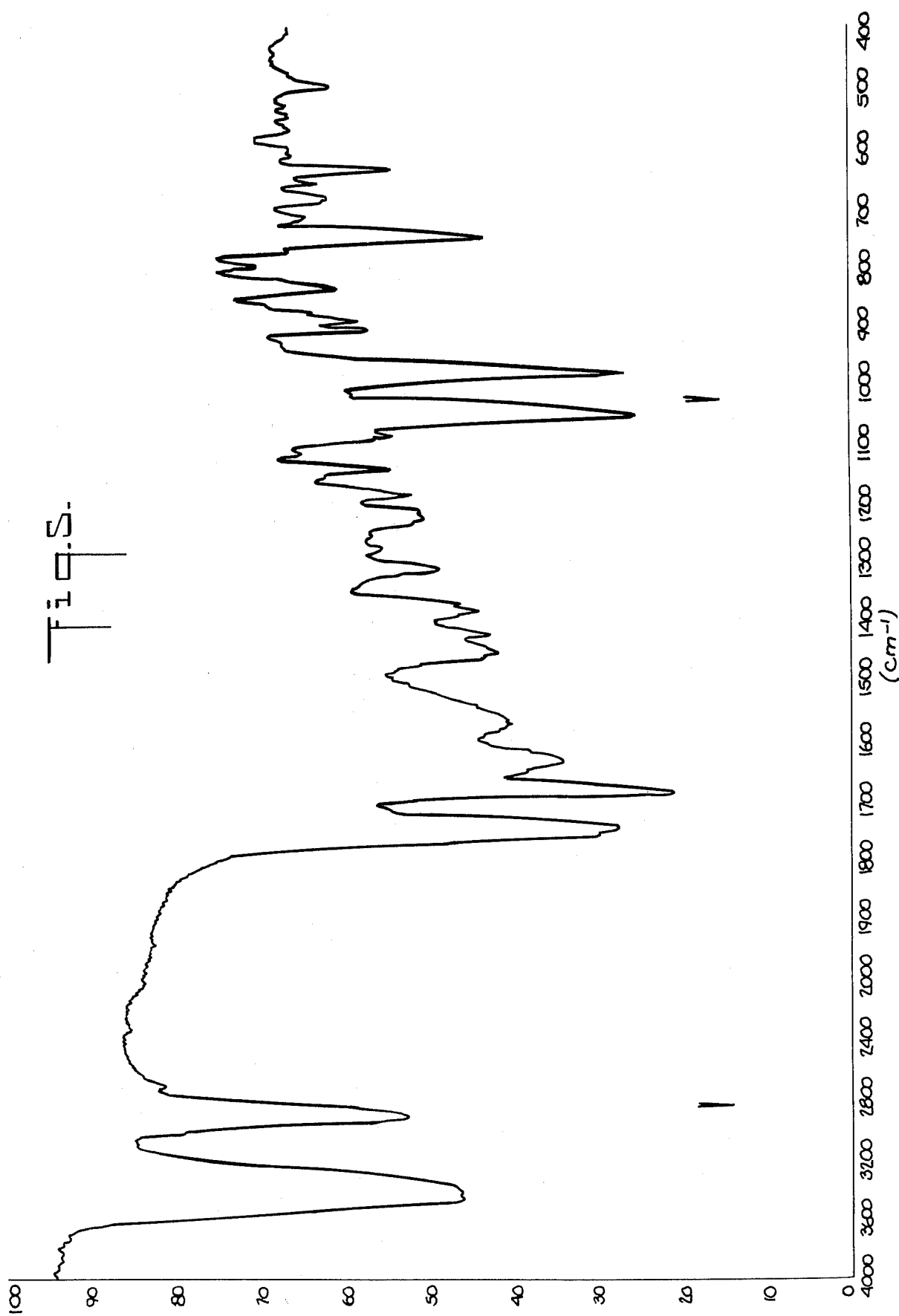
FIG. 5 shows the infrared absorption spectrum of tetronolide (F-2).

(3) IR spectrum (KBr tablet): FIG. 5
(4) PMR spectrum (in $CDCl_3$, internal standard: TMS): FIG. 6
(5) CMR spectrum (in $CDCl_3$, internal standard: TMS): 206.0, 201.0, 191.9, 170.3, 170.2, 166.1, 157.2, 145.2, 141.4, 137.2, 135.7, 126.3, 125.1, 123.6, 117.3, 100.9, 97.7, 90.6, 83.7, 78.5, 77.9, 71.7, 68.6, 54.1, 53.8, 52.7, 51.2, 43.0, 41.9, 41.2, 36.8, 35.9, 31.5(two peaks), 31.0, 30.0, 25.1, 21.9, 21.0, 20.8, 17.0, 16.0, 14.9, 14.3, 13.7

(5) 9,17,21-O-Triacetyl tetronolide (referred to as "Compound F-2 triacetate", hereinafter)

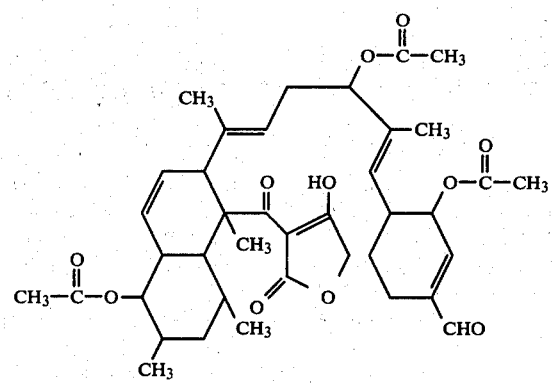

| (1) Elementary analysis: | C (%) | H (%) |
|---|---|---|
| Calculated | 67.24 | 6.83 |
| Found | 67.53 | 6.98 |

Figure 7:
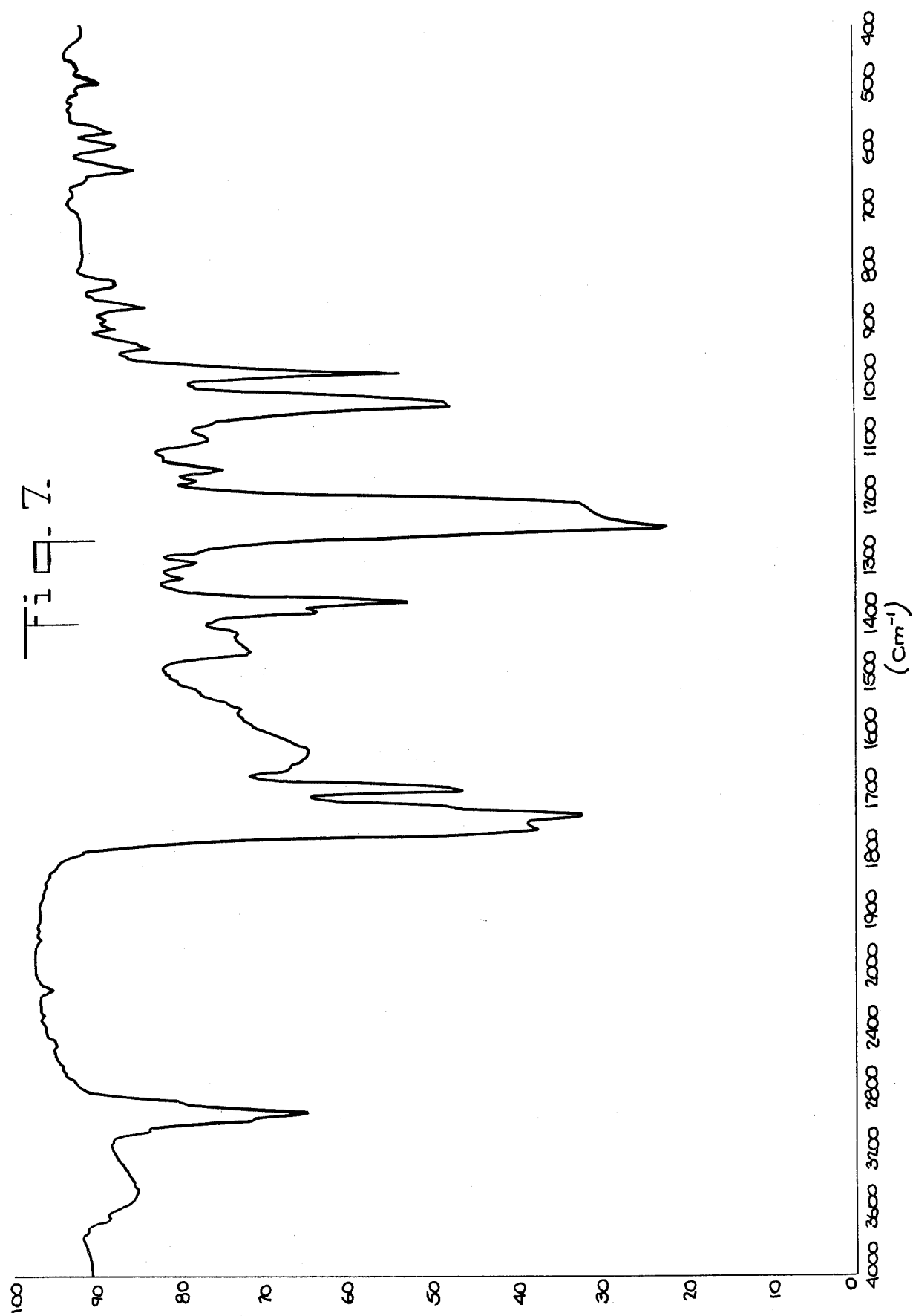
FIG. 7 shows the infrared absorption spectrum of 9,17,21-O-triacetyltetronolide (F-2 triacetate).
Figure 4:
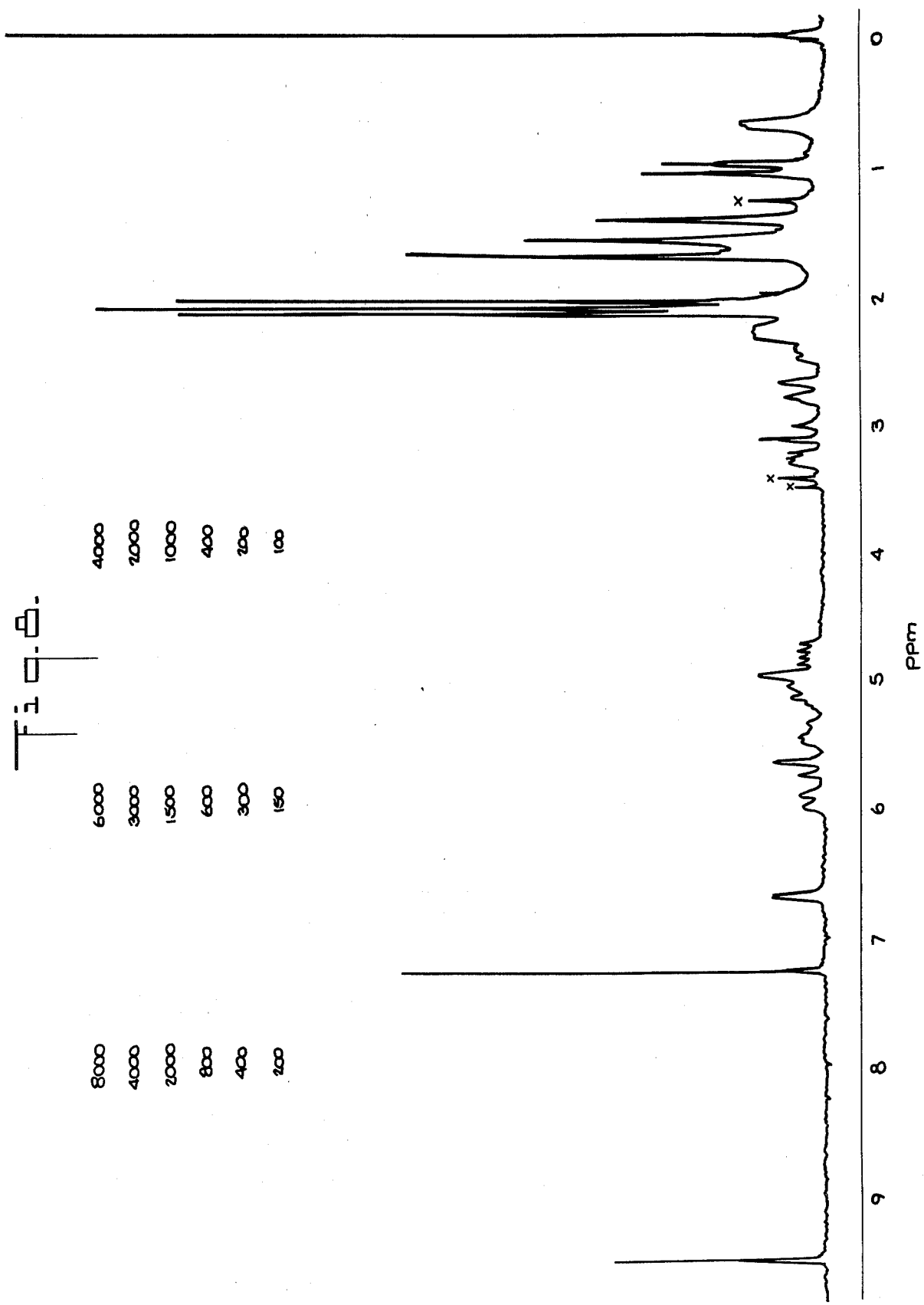

(2) IR spectrum (in $CHCl_3$): FIG. 7
(3) PMR spectrum (in $CDCl_3$, internal standard: TMS): FIG. 8
(4) CMR spectrum (in $CDCl_3$, internal standard: TMS): 206.0, 200.9, 191.7, 170.4, 170.0(two peaks), 166.2, 145.7, 141.5, 137.6, 136.3, 126.3, 125.2, 123.4, 116.1, 100.9, 83.5, 77.9, 73.7, 69.8, 54.2, 51.2, 43.0(two peaks), 41.2, 36.9, 31.6, 31.1, 29.6, 29.5, 21.9, 21.1(two peaks), 20.6, 15.6, 15.0, 14.3, 13.8

Behavior of the tetronolide compounds on thin layer chromatography is shown in the following Table 1. Each tetronolide is distinguished from the tetrocarcins having quite analogous chemical structures.

| Compound | Rf value |
|---|---|
| Tetrocarcin A | 0.57 |
| Tetrocarcin B | 0.52 |
| Tetrocarcin C | 0.56 |
| Tetrocarcin D | 0.53 |
| F-1 | 0.63 |
| F-1 monoacetate | 0.77 |
| F-1 diacetate | 0.85 |
| F-2 | 0.20 |
| F-2 triacetate | 0.80 |

Antibacterial activities of F-1, F-1 monoacetate, F-1 diacetate, F-2 and F-2 triacetate against various microorganisms determined by the agar dilution method at pH 7.0 are shown in the following Table 2.

TABLE 2

| Microorganism | M I C ($\mu$g/ml) | | | | |
|---|---|---|---|---|---|
| | F-1 | F-1 mono-acetate | F-1 di-acetate | F-2 | F-2 tri-acetate |
| Staphylococcus aureus ATCC 6538 P | >200 | 2.0 | 0.8 | >200 | 2.3 |
| Bacillus subtilis No. 10707 | 150 | 12.0 | 6.4 | >200 | 4.6 |
| Klebsiella pneumoniae ATCC 10031 | >200 | >200 | >200 | >200 | >200 |
| Escherichia coli ATCC 26 | >200 | >200 | >200 | >200 | >200 |
| Shigella sonnei ATCC 9290 | >200 | >200 | >200 | >200 | >200 |
| Salmonella typhosa ATCC 9992 | >200 | >200 | >200 | >200 | >200 |

Anti-tumor activities of these tetronolide compounds are as follows: Effect on hepatoma MH-134 of mouse: Six female $C_3H$-strain mice having a weight of about 20 g are used for each group as test animals and $10^6$ cells of hepatoma MH-134 of mouse are implanted in the animal. Twenty-four hours after implantation, 0.2 ml of physiological saline containing a tetronolide compound in various concentrations emulsified with Tween-80 is administered intraperitoneally. Physiological saline comprises 0.8 g/dl NaCl, 0.02 g/dl KCl, 1.15 g/dl $Na_2HPO_4$ and 0.02 g/dl $KH_2PO_4$ (pH 7.2). For comparison, 0.2 ml of physiological saline containing tetrocarcin A is administered to a group of animals intraperitoneally at the same time as the test compound.

Average survival period (ASP: days) and T/C (T: average survival days of the groups administered with test compound, C: that of the control group) are determined. The results are shown in the following Table 3.

TABLE 3

| Test compound | Dosage (mg/kg) | A S P (days) | Anti-tumor effect T/C |
|---|---|---|---|
| Control | 0 | 14.0 | — |
| Tetrocarcin A | 30 | 21.0 | 1.50 |
| | 20 | 22.4 | 1.60 |
| F-1 | 150 | 20.3 | 1.45 |
| | 100 | 19.6 | 1.40 |
| | 50 | 19.6 | 1.40 |
| F-1 diacetate | 70 | 21.0 | 1.50 |
| | 35 | 21.7 | 1.55 |
| F-2 | 150 | 14.0 | 1.00 |
| | 100 | 16.8 | 1.20 |
| | 50 | 14.0 | 1.00 |
| F-2 triacetate | 70 | 20.3 | 1.45 |
| | 35 | 18.2 | 1.30 |

The acute toxicity ($LD_{50}$) of the tetronolide compounds are shown below. $LD_{50}$ of F-1, F-1 diacetate, F-2 and F-2 triacetate are about 220 mg/kg, 110 mg/kg, 220 mg/kg and 110 mg/kg respectively when those test compounds are administered intraperitoneally to the mice according to Litchfield-Wilcoxon method. As is apparent from the foregoing, the tetronolide compounds are useful as both an anti-tumor agent and an antibacterial agent as well as tetrocarcins.

Furthermore, as is apparent from the chemical structre of F-2, F-2 is useful as an intermediate in order to prepare F-1 and derivatives of F-2. As an anti-tumor agent, novel compounds of the present invention are most suitably administered as an injection intravenously or intraperitoneally. They may be effectively administered on a daily basis in dosages of from about 0.2 to 0.5 mg/kg of human body weight.

Preparation methods for the present tetronolide compounds are explained below. Among the tetronolide compounds, the compounds having OH group at the 9-, 17- or 21-position such as, tetronolide (Compound F-2), 17-O-tetronitrosyl tetronolide (F-1), etc. are obtained from the culture liquor of microorganisms. Compound F-1 and/or F-2 are obtained by culturing a microorganism belonging to the genus Micromonospora and capable of producing F-1 and/or F-2 in a nutrient medium, accumulating F-1 and/or F-2 in the culture liquor and recovering F-1 and/or F-2 therefrom.

Any microorganism belonging to the genus Micromonospora and capable of producing F-1 and/or F-2 may be used in the present invention. A particularly preferred strain is *Micromonospora chalcea* KY 11091. The strain has been deposited with the Fermentation Research Institute, Japan and assigned the registered number FERM-P No. 4458. The strain has also been deposited with the culture collection of the Northern Utilization Research and Development Division, Agricultural Research Service, U.S. Department of Agricultural under culture No. NRRL 11289.

Properties of the strain, which are described in Japanese Patent Application No. 45916/78 (Japanese Published Unexamined Patent Application No. 138501/79, U.S patent application Ser. No. 31,912) and Japanese patent application Nos. 152253/79, 17498/80 and 24926/80, are set forth below. The strain has been deposited as Micromonospora sp. KY 11091 and the name has been changed to *Micromonospora chalcea* KY 11091 after identification.

KY 11091 strain is characterized by the following properties:

I. Morphology:

KY 11091 does not form true aerial mycelia on an agar medium as seen in the case of a microorganism belonging to the genus Streptomyces, etc. and forms a brick-red, glossy, waxy spore layer on an agar medium on which spores are readily formed.

When the strain is cultured in a liquid medium, the growth is initially bright orange changing to brown to dark brown at the later stages. Many spores are formed.

Microscopic observation shows that mycelia having a diameter of about $0.5\mu$ are well developed and septa are not formed. A single spore is produced at the end of sporophore (about $0.3-1.0\mu$ in length) branched from the substrate mycelium. Many spores are formed along the mycelia. Matured spores have a diameter of about $1.0\mu$ and are spherical in shape.

II. Culture Characteristics

The degree of growth, color of substrate mycelium and soluble pigments when KY 11091 strain is cultured on various media are shown in the following Table 5. The color indications are given according to the classifications in the Color Harmony Manual, (Container Corporation of America).

TABLE 5

| Medium | Growth | Color | Soluble Pigments |
|---|---|---|---|
| Sucrose-Nitrate agar | Good, flat | Black-olive (1 po) | None |
| Glucose-Asparagine agar | Poor, flat | Black-olive (1 po) | None |
| Glycerin-Asparagine agar | Poor, flat | White (a) | None |
| Starch-Inorganic salt agar | Good, flat | Black-olive (1 po) | None |
| Tyrosine agar | Moderate | Black-olive (1 po) | None |
| Nutrient agar | Moderate, flat | Apricot (4 ca) | None |
| Oatmeal agar | Moderate, flat | Apricot (4 ca) | None |
| Yeast-Malt extract agar | Good, raised | Black-olive (1 po) | None |
| Peptone-Yeast extract-Iron agar | Moderate, flat | Orange (4 la) | None |

III. Physiological Characteristics

The physiological characteristics of KY 11091 strain are illustrated in the following Table 6 in which the optimum temperature is determined after 5 days of culturing and the action upon milk and the decomposition of cellulose are observed after one month of culturing. The other observations are based on culturing at 27° C. for two weeks.

TABLE 6

| (1) Utilization of Carbon Sources | |
|---|---|
| Carbon Source | Utilization |
| D-Arabinose | − |
| D-Xylose | + |
| D-Glucose | ++ |
| D-Fructose | + |
| Sucrose | ++ |
| Inositol | − |
| L-Rhamnose | − |
| Raffinose | ++ |
| D-Mannitol | − |
| Ribose | + |
| Salicin | + |
| L-Arabinose | + |
| Glycerol | ± |
| Melibiose | + |
| (2) Liquefaction of gelatin | Weakly positive |
| (3) Liquefaction of milk | Positive |
| Peptonization of milk | Weakly positive |
| (4) Decomposition of cellulose | Little |
| (5) Hydrolysis of starch | Positive |
| (6) Optimum growth pH | 6.6–7.5 |
| (7) Optimum growth temperature | 28–38° C. |
| (8) Formation of tyrosinase | None |
| (9) Formation of melanoid pigments | None |

As apparent from the above observations, the Ky 11091 strain is a mesophile which does not form true aerial mycelia on agar medium and forms a single spore on substrate mucelia. By analysis of cell wall, it is determined that the strain contains mesodiaminopimelic acid. Accordingly, the Ky 11091 strain is classified as belonging to the genus Micromonospora.

KY 11091 the strain is identified as belonging to *Micromonospora chalcea* based on the description mentioned above and those in Bergey's Manual of Determinative Bacteriology 8th Edition, p. 846–849 and International Journal of Systematic Bacteriology Vol. 21, No. 3, p. 248–253 and the strain is named *Micromonospora chalcea* KY 11091.

As is the case with other known strains belonging to the genus Micromonospora, the microorganism capable of producing F-1 and/or F-2 can be mutated by artificial means such as ultra-violet irradiation, X-ray irradiation and the treatment with various mutation-inducing chemical. Any strain, even if thus mutated, is contemplated as appropriate for the present invention insofar as it has the ability to produce F-1 and/or F-2.

Methods for culturing are described below.

Conventional methods for culturing Actinomycetes may be employed in the process of the present invention. Thus, various nutrient sources may be used for the culture medium. Appropriate carbon sources include glucose, starch, dextrin, mannose, fructose, sucrose and molasses either alone or in combination. Hydrocarbons, alcohols, organic acids, etc. may also be used depending upon the assimilability possessed by the microorganisms to be used. As inorganic and organic nitrogen sources, ammonium chloride, ammonium sulfate, ammonium nitrate, sodium nitrate, urea or natural nitrogen sources such as peptone, meat extract, yeast extract, dry yeast, corn steep liquor, soybean powder and casamino acid, soluble vegetable protein, may be used either alone or in combination. If necessary, inorganic salts such as sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate, copper sulfate, etc. may be added to the medium. Moreover, organic and inorganic materials such as vitamin $B_1$, biotin, etc. which promote the growth of the particular strain and enhance the production of F-1 and/or F-2 may be added to the medium.

As a culturing method, a liquid culturing method, particularly a submerged stirring culturing method is most suitable. Culturing temperature is 25°–40° C., preferably 28°–38° C., and the pH is controlled at 4–10, preferably 6–8 with aqueous ammonia, ammonium carbonate solution, etc. Usually, after 1 to 7 days of liquid culturing, the desired compound(s) are formed and accumulated in the culture liquor. When the yield of the desired compound(s) in the culture liquor reaches a maximum, culturing is discontinued and the desired product(s) are isolated and purified from the culture liquor after the microbial cells have been removed by filtration.

Isolation and purification of F-1 and/or F-2 are carried out by methods usually used for the isolation and purification of microbial metabolic products from a culture liquor. For example, the cell-free culture filtrate (pH 6.0) is passed through a column packed with non-ionic porous resin such as HP-20 (trademark, Mitsubishi Chemical Industries) to adsorb active principles, and the active principles are desorbed using methanol, acetone, ethyl acetate, or the like. The resultant eluant is concentrated to dryness and the residue is dissolved in water. Then the solution is passed through a column packed with active carbon and elution is carried out with an organic solvent such as ethyl acetate, acetone, etc. The eluate is concentrated to dryness and the residue is dissolved in chloroform. The solution is passed through a column packed with silica gel suspended in chloroform. By passing chloroform through the column, impurities are removed. Elution is carried out with a mixed solvent of chloroform and methanol (99:1 by volume), and the eluate is concentrated to dryness to obtain the Compound F-1.

Elution is then carried out with a mixed solvent of chloroform and methanol (98:2 by volume) to obtain the eluate containing the mixture of tetrocarcins A, B, C and D. Thereafter, elution is carried out with a mixed solvent of chloroform and methanol (95:5 by volume) to obtain the eluate containing Compound F-2.

On the other hand, it is possible to isolate F-1 and F-2 using thin layer chromatography of silica gel. Further, purified F-1 and F-2 are obtained by repeating the above-mentioned chromatography or using a column packed with Sephadex LH-20 (Pharmacia Fine Chemicals, Inc. Sweden).

Methods for preparing F-1 and F-2 by hydrolysis of tetrocarcins are described below.

(A) Method for preparing F-1

Tetrocarcin A, B or C or a mixture thereof in any combination is hydrolyzed in a mixture of an acid such as hydrochloric acid and sulfuric acid and an organic solvent such as acetone. After hydrolysis, the solvent is distilled away and the resulting aqueous solution is extracted with chloroform. The chloroform layer is concentrated and subjected to silica gel chromatography to obtain F-1 fractions.

(B) Method for preparing F-2

F-1 or tetrocarcin A, B, C or D or a mixture of the tetrocarcins in any combination is hydrolyzed in a mixture of an acid such as hydrochloric acid and sulfuric acid and an organic solvent such as acetone and methanol. The acid is used in a higher concentration than in the preparation of F-1. After hydrolysis, the solvent is distilled away and the resulting aqueous solution is extracted with chloroform or ethyl acetate. The organic solvent layer is concentrated and subjected to silica gel column chromatography to obtain F-2 fractions.

Acyl derivatives of tetronolide compounds, that is, F-1-21-O-acetate, F-1-21-O-propionate, F-1-21-O-n-butylate, F-1 diacetate, F-1 dipropionate, F-2 triacetate, F-2 tripropionate and F-2 tri-n-butylate, etc., can be obtained by acylating tetronolide compounds using conventional acylating agents.

For example, they are obtained by acylation with acid anhydrides. After reaction, acyl derivatives are isolated by a method usually used in organic synthetic chemistry. That is, purification is carried out by a combination of operations such as concentration, recrystallization and chromatography.

F-1 monoacetate can be obtained by hydrolysis of tetrocarcin A acetate.

Process for producing the compounds of the present invention is specifically shown by the following examples. In the examples, the behavior of the compounds is monitored by bioassay using *Bacillus subtilis* No. 10707 or TLC chromatoscanner method (Shimazu Chromatoscanner CS 910) (ultraviolet reflection method, double beam, single scan, wavelength sample 260 nm, reference 350 nm).

EXAMPLE 1

In this example, *Micromonospora chalcea* KY 11091 (FERM-P No. 4458, NRRL No. 11,289) is used as a seed strain.

The strain is inoculated into 300 ml of seed medium comprising 4 g/l KCl, 0.5 g/l $MgSO_4.7H_2O$, 1.5 g/l $KH_2PO_4$, 5.0 g/l $(NH_4)_2SO_4$, 20 g/l sucrose, 10 g/l fructose, 10 g/l glucose, 5.0 g/l corn steep liquor and 20 g/l CaCO$_3$ (pH 7.0) in a 2 l-Erlenmeyer flask and cultured at 30° C. with shaking (220 r.p.m.) for 48 hours. The thus obtained seed culture is transferred at a rate of 5% (volume) into a 30 l-jar fermenter containing 15 l of a fermentation medium comprising 60 g/l soluble starch, 10 g/l defatted soybean meal, 10 g/l peptone, 0.5 g/l K$_2$HPO$_4$, 0.5 g/l MgSO$_4$.7H$_2$O and 1 g/l CaCO$_3$. The pH of the medium is adjusted to 7.2 with NaOH before sterilization. Culturing is carried out at 30° C. with aeration and agitation (15 l/min, 250 r.p.m) for 72 hours without controlling the pH of the medium. The resulting culture liquor is filtered to remove cell bodies and precipitates and to obtain 13 l of filtrate. The filtrate is passed through a column packed with 1 l of non-ionic porous resin (trademark "HP-10", a product of Mitsubishi Chemical Industries) to adsorb the active principles. Then, the resin is washed with water and 30% (V/V) aqueous acetone to remove the impurities. Elution is carried out with acetone and the acetone fractions are concentrated to dryness to obtain a residue which is then dissolved in 30% (V/V) aqueous acetone. The resultant solution is charged on a column packed with 500 ml of active carbon for adsorption and the carbon is washed with 30% (V/V) aqueous acetone. Elution is carried out with acetone, whereby most of the pigments which are present in the solution as impurities is removed. Active fractions are concentrated to dryness and the residue is dissolved in a small amount (about 10 ml) of chloroform. The chloroform solution is gently charged on a column packed with 500 ml of silica gel [trademark: silica gel for chromatography (100–200 mesh), a product of Kanto Kagaku, the same shall apply hereinafter] suspended in advance in chloroform and then thoroughly washed with about 2 l of chloroform. Elution is carried out with a mixed solvent of chloroform and methanol (99:1) to obtain active fractions containing F-1. Then, elution is carried out with a mixed solvent of chloroform and methanol (98:2) to obtain active fractions containing tetrocarcins A, B, C and D. For further purification, the fractions containing F-1 are concentrated to dryness and the residue is dissolved in a small amount of chloroform. The resulting solution is gently charged on a column packed with 250 ml of silica gel which is in advance suspended in chloroform and subjected to chromatography using chloroform and methanol (99:1).

Each of the thus obtained F-1 fractions is concentrated to dryness and the residue is dissolved in acetone. The resulting solution is subjected to silica gel thin layer chromatography using chloroform and methanol (9:1) as the developing solvent. Elution is carried out with the developing solvent or acetone and the eluate is concentrated to dryness to obtain a residue which is then dissolved in ethyl acetate. The resulting solution is mixed with 0.1 N HCl by shaking and the solvent layer is concentrated to dryness to obtain a powdery product. This product may be redissolved in ethyl acetate and then precipitated with hexane to obtain a powder. Thus, about 5 mg of F-1 is obtained and the physicochemical properties, antibacterial activity and anti-tumor activity thereof are described hereinbefore.

EXAMPLE 2

In this example, culturing is carried out in the same manner as in Example 1 for 72 hours without controlling the pH of the medium. The resulting culture liquor is filtered to remove cell bodies and precipitates and to obtain 13 l of filtrate. The filtrate is passed through a column packed with 1 l of non-ionic porous resin (trademark "HP-10", a product of Mitsubishi Chemical Industries) to adsorb the active principles. Then, the resin is washed with water and 30% (V/V) aqueous acetone to remove the impurities. Elution is carried out with acetone and the acetone fractions are concentrated to dryness to obtain a residue which is then dissolved in 30% (V/V) aqueous acetone. The resultant solution is charged on a column packed with 500 ml of active carbon for adsorption and the carbon is washed with 30% (V/V) aqueous acetone. Elution is carried out with acetone, whereby most of the pigments which are present in the solution as impurities is removed. Active fractions are concentrated to dryness and the residue is dissolved in a small amount (about 10 ml) of chloroform. The chloroform solution is gently charged on a column packed with 500 ml of silica gel [trademark: silica gel for chromatography (100–200 mesh), a product of Kanto Kagaku, the same shall apply hereinafter] suspended in advance in chloroform and then thoroughly washed with about 2 l of chloroform. Elution is carried out with chloroform and methanol (99:1) and the eluate is removed. Then, elution is carried out with chloroform and methanol (98:2) to elute the active fractions containing tetrocarcins A, B, C and D. By the subsequent elution with chloroform and methanol (95:5), the fractions containing F-2 are eluted. For further purification, the fractions containing F-2 are concentrated to dryness and the residue is dissolved in a small amount of chloroform. The resulting solution is gently charged on a column packed with 250 ml of silica gel which is in advance suspended in chloroform and subjected to chromatography using chloroform and methanol (9:1). Each of the thus obtained F-2 fractions is concentrated and the residue is dissolved in acetone. The resulting solution is subjected to silica gel thin layer chromatography using chloroform and methanol (9:1) as the developing solvent. Elution is carried out with the developing solvent or acetone and the eluate is concentrated to dryness to obtain a residue which is then dissolved in ethyl acetate. The resulting solution is mixed with 0.1 N HCl by shaking and the solvent layer is concentrated to dryness to obtain a powdery product. This product may be redissolved in ethyl acetate and then precipitated with hexane to obtain a powder. Thus, about 3 mg of F-2 is obtained and the physicochemical properties, antibacterial activity and anti-tumor activity thereof are as described hereinbefore.

EXAMPLE 3

In this example culturing is carried out in the same manner as in Example 1 except that a fermentation medium having the following composition is used. Composition of the fermentation medium:

| | |
|---|---|
| Soluble starch | 40 g/l |
| Defatted soybean meal | 30 g/l |
| Dextrin | 5 g/l |
| Corn steep liquor | 5 g/l |
| K$_2$HPO$_4$ | 0.5 g/l |
| MgSO$_4$.7H$_2$O | 0.5 g/l |
| CaCO$_3$ | 1 g/l |

The pH of the medium is adjusted to 7.0 with NaOH before sterilization. Culturing and purification are carried out in the same manner as in Example 1, whereby about 8 mg of F-1 is obtained. The physicochemical properties, antibacterial activity and anti-tumor activity of the obtained F-1 agree well with those of the product in Example 1.

EXAMPLE 4

In this example, culturing is carried out in the same manner as in Example 2 except that a fermentation medium having the following composition is used.
Composition of the fermentation medium:

| Soluble starch | 40 g/l |
|---|---|
| Defatted soybean meal | 30 g/l |
| Dextrin | 5 g/l |
| Corn steep liquor | 5 g/l |
| $K_2HPO_4$ | 0.5 g/l |
| $MgSO_4.7H_2O$ | 0.5 g/l |
| $CaCO_3$ | 1 g/l |

The pH of the medium is adjusted to 7.0 with NaOH before sterilization. Culturing and purification are carried out in the same manner as in Example 2, whereby about 5 mg of F-2 is obtained. The physicochemical properties, antibacterial activity and anti-tumor activity of the obtained F-2 agree well with those of the product in Example 2.

EXAMPLE 5

In this example, 5.1 g of DC-11 (tetrocarcin A) obtained by a similar method to that described in Japanese Published Unexamined Application No. 138501/79 is dissolved in 500 ml of acetone and 250 ml of 0.2 N HCl aqueous solution is added thereto, followed by boiling for 15 hours. Acetone in the reaction solution is distilled away under reduced pressure and the aqueous solution is extracted with chloroform. The chloroform layer is washed with water, dried over $Na_2SO_4$ and then subjected to silica gel column chromatography. Elution is carried out with chloroform and methanol (97:3). The fractions containing F-1 are combined and the solvent is distilled away. The residue is dissolved in a small amount of ethyl acetate and precipitated with hexane, whereby 3.5 g of white powder of F-1 is obtained.

EXAMPLE 6

In this example, 2.5 g of tetrocarcin A is dissolved in 250 ml of methanol and 150 ml of 2 N HCl aqueous solution is added thereto, followed by boiling for 25 hours. Methanol is distilled away under reduced pressure and the aqueous solution is extracted with chloroform. The chloroform layer is washed with water, dried over $Na_2SO_4$ and subjected to silica gel column chromatography. Elution is carried out with a mixed solvent of chloroform and methanol in the ratio of 95:5 to elute F-1 and then with a mixed solvent of chloroform and methanol in the ratio of 9:1 to elute F-2. The eluted F-1 is purified in the same manner as in Example 5, whereby 205 mg of white powder of F-1 is obtained. The eluted F-2 is dissolved in 100 ml of ethyl acetate containing a small amount of pyridine and washed with 50 ml of 1 N HCl. Then the ethyl acetate layer is washed with water and dried over $Na_2SO_4$, followed by removal of the solvent by distillation under reduced pressure. By recrystallization from chloroform, 430 mg of white plates of F-2 is obtained.

EXAMPLE 7

In this example, 358 mg of F-1 is dissolved in 35 ml of methanol and 7 ml of chloroform. To the solution is added 10 ml of 12 N $H_2SO_4$ and the mixture is boiled for 32 hours. After extraction with chloroform, the chloroform layer is washed with water and dried over $Na_2SO_4$. Chloroform is distilled away under reduced pressure and the residue is subjected to silica gel column chromatography. Elution is carried out with chloroform and methanol (9:1) to elute the fractions containing F-2. By the same treatment as in Example 6, 150 mg of white plates of F-2 is obtained.

EXAMPLE 8

In this example, 500 mg of F-1 is dissolved in 1.5 ml of anhydrous pyridine and 0.5 ml of acetic anhydride is added thereto, followed by stirring at room temperature for 15 hours. The reaction mixture is mixed with toluene and dried under reduced pressure. The residue is subjected to silica gel column chromatography and elution is carried out with chloroform and methanol (98:2). The fractions containing F-1 diacetate are combined and the solvent is distilled away under reduced pressure. By recrystallization from n-hexane-acetone, 97 mg of white needles of F-1 diacetate is obtained.

The physicochemical properties, antibacterial activity and anti-tumor activity of the product are as described hereinbefore.

EXAMPLE 9

In this example, 174 mg of F-2 is dissolved in 6 ml of anhydrous pyridine and 0.6 ml of acetic anhydride is added thereto, followed by stirring at room temperature for 23 hours. The reaction mixture is mixed with toluene and dried under reduced pressure. The residue is subjected to silica gel column chromatography and elution is carried out with chloroform and methanol (98:2). The fractions containing F-2 triacetate are combined and the solvent is distilled away under reduced pressure. By recrystallization from n-hexane-acetone, 95 mg of white prisms of F-2 triacetate is obtained. The physicochemical properties, antibacterial activity and anti-tumor activity of the product are as described hereinbefore.

EXAMPLE 10

In this example, 105 mg of tetrocarcin A acetate obtained by the same procedure as in Example 8 or 9 except using tetrocarcin A is dissolved in 11 ml of acetone and 5 ml of 0.2 N HCl is added thereto, followed by boiling for 6.5 hours. Acetone is distilled away under reduced pressure and the residue is extracted with chloroform. The chloroform layer is washed with water and dried over $Na_2SO_4$. Then, chloroform is distilled away under reduced pressure and the residue is subjected to silica gel column chromatography. Elution is carried out with chloroform and methanol (98:2) to obtain the fractions containing F-1 monoacetate. The eluted F-1 monoacetate is dissolved in a small amount of ethyl acetate and precipitated with hexane, whereby 22 mg of white powder of F-1 monoacetate is obtained. The physicochemical properties, antibacterial activity, etc. of the product are a described hereinbefore.

EXAMPLE 11

Preparation of anti-tumor injection

In this example, 10 mg of F-1 or F-2 obtained as in Example 1 or 2 is dissolved in 50 ml of ethanol and 30 mg of HCO-60 (Nikkol, a product of Nikko Chemicals Co., Ltd.) is added thereto. After stirring, ethanol is removed by suction. To the residue is added about 10 ml of sterilized physiological saline solution to make an injection preparation.

An injection can also be prepared by adding about 10 ml of sterilized physiological saline solution to 10 mg of a pharmaceutically acceptable salt of F-1 or F-2, for example, sodium salt of F-1 or F-2 obtained according to the method for preparing sodium salt of tetrocarcin A (DC-11) described in Japanese patent application No. 42936/80 filed by the present Applicant.

Further, an injection preparation can be prepared by treating derivatives of F-1 and F-2 as above.

REFERENCE EXAMPLE 1

In this example, *Micromonospora chalcea* KY 11091 (FERM-P No. 4458, NRRL No. 11,289) is used as a seed strain.

The strain is inoculated into 300 ml of seed medium comprising 4 g/l KCl, 0.5 g/l $MgSO_4.7H_2O$, 1.5 g/l $KH_2PO_4$, 5.0 g/l $(NH_4)_2SO_4$, 20 g/l sucrose, 10 g/l fructose, 10 g/l glucose, 5.0 g/l corn steep liquor and 20 g/l $CaCO_3$ (pH 7.0) in a 2 l-Erlenmeyer flask and cultured at 30° C. with shaking (220 r.p.m.) for 48 hours. The thus obtained seed culture is transferred at a rate of 5% (volume) into a 30 l-jar fermenter containing 15 l of a fermentation medium comprising 60 g/l soluble starch, 10 g/l defatted soybean meal, 10 g/l peptone, 0.5 g/l $K_2HPO_4$, 0.5 g/l $MgSO_4.7H_2O$ and 1 g/l $CaCO_3$. The pH of the medium is adjusted to 7.2 with NaOH before sterilization. Culturing is carried out at 30° C. with aeration and agitation (15 l/min, 250 r.p.m.) for 72 hours without controlling the pH of the medium. The resulting culture liquor is filtered to remove cell bodies and precipitates and to obtain 13 l of filtrate. The filtrate is passed through a column packed with 1 l of non-ionic porous resin (trademark "HP-10", a product of Mitsubishi Chemical Industries) to adsorb the active principles. Then, the resin is washed with water and 30% (V/V) aqueous acetone to remove the impurities. Elution is carried out with acetone and the acetone fractions are concentrated to dryness to obtain a residue which is then dissolved in 30% (V/V) aqueous acetone. The resultant solution is charged on a column packed with 500 ml of active carbon for adsorption and the carbon is washed with 30% (V/V) aqueous acetone. Elution is carried out with acetone, whereby most of the pigments which are present in the solution as impurities is removed. Active fractions are concentrated to dryness and the residue is dissolved in a small amount (about 10 ml) of chloroform. The chloroform solution is gently charged on a column packed with 500 ml of silica gel [trademark: silica gel for chromatography (100~200 mesh), a product of Kanto Kagaku, the same shall apply hereinafter] suspended in advance in chloroform and then thoroughly washed with about 2 l of chloroform. Elution is carried out with a mixed solvent of chloroform and methanol (98:2, by volume) to obtain active fractions containing DC-11 and DC-11-A-3. Then, the fractions containing DC-11 and DC-11-A-3 are concentrated to dryness and the residue is dissolved in toluene and acetone (2:1, by volume). The resulting solution is gently charged on a column packed with 250 ml of silica gel which is in advance suspended in toluene and acetone (2:1, by volume) and subjected to chromatography using the same mixed solvent to elute first DC-11 and then DC-11-A-3, and this chromatography procedure is repeated twice. The fractions containing DC-11 and the fractions containing DC-11-A-3 are concentrated to dryness separately to obtain 25 mg of DC-11 and 5 mg of DC-11-A-3.

The physicochemical properties of DC-11-A-3 are as follows.

(1) Melting point: 187°–190° C.

| (2) Elementary analysis: | H (%) | C (%) | N (%) |
|---|---|---|---|
| | 7.01 | 59.33 | 1.90 |

(3) CMR spectrum (in $CDCl_3$, internal standard: TMS) (δ ppm):

206.2, 201.3, 192.4, 170.7, 170.0, 166.5, 157.2, 149.4, 141.3, 136.2, 135.9, 126.1, 123.0, 118.2, 100.8, 99.2, 98.7, 96.3, 92.5, 91.9, 91.4, 84.7, 83.9, 81.1, 77.8, 75.2, 71.6, 70.2, 69.2, 68.0, 67.7, 66.4, 64.4, 63.8, 63.3, 54.2, 53.7, 52.8, 51.2, 44.8, 43.2, 41.5, 38.4, 37.0, 35.9, 34.3, 31.1, 30.7, 29.7, 27.3, 26.3, 25.3, 21.9, 20.8, 20.7, 18.8, 18.0, 17.7, 16.9, 16.0, 15.0, 14.3, 13.9

(4) Specific optical rotation:
$[\alpha]_D^{22} = -62.5°$ (c=1.0, chloroform)

(5) Solubility

DC-11-A-3 is soluble in methanol, ethanol, butanol, acetone, ethyl acetate and chloroform, slightly soluble in benzene and water, and insoluble in petroleum ether and n-hexane.

The Rf values of DC-11 and DC-11-A-3 in silica gel thin layer chromatography are set forth in the following Table.

TABLE

| Developer | Compound | Rf value |
|---|---|---|
| (1) Rf values obtained using silica gel plate (Trademark: DC-Fertigplatten Kieselgel $60F_{254}$, E. Merck) | | |
| I. toluene:acetone | DC-11 | 0.47 |
| = 20:30 (by volume) | DC-11-A-3 | 0.44 |
| II. benzene:acetone | DC-11 | 0.54 |
| = 20:30 (by volume) | DC-11-A-3 | 0.50 |
| III. acetic acid:ethyl acetate | DC-11 | 0.31 |
| = 1:20 (by volume) | DC-11-A-3 | 0.27 |
| (2) Rf values obtained using silica gel plate (Trademark: DC-Fertigplatten Kieselgel $60F_{254}$ Silanisiert, E. Merck) | | |
| I. chloroform:dioxane | DC-11 | 0.60 |
| = 95:5 (by volume) | DC-11-A-3 | 0.57 |
| II. n-hexane:ethyl acetate | DC-11 | 0.60 |
| = 10:20 (by volume) | DC-11-A-3 | 0.50 |

As is the case with DC-11, DC-11-A-3 does not show clear parent ion in Mass Spectroscopic spectrum. However, taking the results of elementary analysis and CMR into consideration, it seems reasonable that DC-11-A-3 is a compound represented by the molecular formula: $C_{66-72}H_{96-102}N_2O_{22-28}$ and having the molecular weight: 1268–1442. It is apparent from the above physicochemical properties that DC-11-A-3 is different from DC-11 disclosed in Japanese Patent Application No. 45916/78.

In the above application, the Applicant made the minor amendments and supplements relating to the physicochemical properties of DC-11 on Jan. 25, 1980. DC-11-A-3 is different from DC-11 after the said amendment and from DC-11-A-2 disclosed in the application (title: "DC-11-A-2") filed by the same applicant on the same day with the present application. Therefore, DC-11-A-3 is a novel compound.

REFERENCE EXAMPLE 2

In this example, *Micromonospora chalcea* KY 11091 (FERM-P No. 4458, NRRL No. 11,289) is used as a seed strain.

The strain is inoculated into 300 ml of seed medium comprising 4 g/l KCl, 0.5 g/l $MgSO_4.7H_2O$, 1.5 g/l $KH_2PO_4$, 5.0 g/l $(NH_4)_2SO_4$, 20 g/l sucrose, 10 g/l fructose, 10 g/l glucose, 5.0 g/l corn steep liquor and 20 g/l $CaCO_3$ (pH 7.0) in a 2 l-Erlenmeyer flask and cultured at 30° C. with shaking (220 r.p.m.) for 48 hours. The thus obtained seed culture is transferred at a rate of 5% (volume) into a 30 l-jar fermenter containing 15 l of a fermentation medium comprising 60 g/l soluble starch, 10 g/l defatted soybean meal, 10 g/l peptone, 0.5 g/l $K_2HPO_4$, 0.5 g/l $MgSO_4.7H_2O$ and 1 g/l $CaCO_3$. The pH of the medium is adjusted to 7.2 with NaOH before sterilization. Culturing is carried out at 30° C. with aeration and agitation (15 l/min, 250 r.p.m.) for 72 hours without controlling the pH of the medium. The resulting culture liquor is filtered to remove cell bodies and precipitates and to obtain 13 l of filtrate. The filtrate is passed through a column packed with 1 l of non-ionic porous resin (trademark "HP-10", a product of Mitsubishi Chemical Industries) to adsorb the active principles. Then, the resin is washed with water and 30% (V/V) aqueous acetone to remove the impurities. Elution is carried out with acetone and the acetone fractions are concentrated to dryness to obtain a residue which is then dissolved in 30% (V/V) aqueous acetone. The resultant solution is charged on a column packed with 500 ml of active carbon for adsorption and the carbon is washed with 30% (V/V) aqueous acetone. Elution is carried out with acetone, whereby most of the pigments which are present in the solution as impurities is removed. Active fractions are concentrated to dryness and the residue is dissolved in a small amount (about 10 ml) of chloroform. The chloroform solution is gently charged on a column packed with 500 ml of silica gel [trademark: silica gel for chromatography (100–200 mesh), a product of Kanto Kagaku, the same shall apply hereinafter] suspended in advance in chloroform and then thoroughly washed with about 2 l of chloroform. Elution is carried out with a mixed solvent of chloroform and methanol (98:2, by volume) to obtain active fractions containing DC-11 and DC-11-A-3. DC-11-A-2 is eluted with DC-11 and DC-11-A-3 in the latter part of the above fractions. The fractions containing DC-11-A-2 are combined and concentrated to dryness. The residue is gently charged on a column packed with 250 ml of silica gel which is in advance suspended in chloroform. Elution is again carried out with a mixed solvent of chloroform and methanol (98:2, by volume). In this procedure, the fractions containing mainly DC-11-A-2 are combined and concentrated to dryness. The residue is dissolved in acetone. Then, the solution is subjected to silica gel thin layer chromatography using a developer comprising chloroform and methanol (9:1, by volume) to isolate DC-11 contained in the residue as impurities. The desired product is eluted from the silica gel using acetone. Then, the eluates are concentrated to dryness and the residue is dissolved in ethyl acetate. The solution is mixed with 0.1 N HCl by shaking and the solvent layer is concentrated to dryness. The concentrate is dissolved in ethyl acetate and precipitated with hexane to obtain about 5 mg of powder of DC-11-A-2.

The physicochemical properties of the thus obtained DC-11-A-2 are as follows.

(1) Melting point: 192°–196° C.

(2) Elementary analysis:
C=60.8%; H=7.4%; N=2.3%.

(3) Infrared absorption spectrum (KBr tablet) $cm^{-1}$: 3430, 2920, 1760, 1731, 1687, 1630, 1540, 1448, 1375, 1364, 1230, 1117, 1049, 1004, 982

(4) Ultraviolet absorption spectrum (in 90% methanol): λmax: nm($E_{1\ cm}^{1\%}$): 236 sh (149), 268(90), 280 sh (75)

(5) PMR spectrum (in $CDCl_3$, internal standard: TMS)
δ(ppm): 9.58, 6.92, 5.82-4.10 (many peaks), 3.72, 3.67-2.20 (many peaks), 2.09, 1.85, 1.63, 1.60, 1.53, 1.36, 1.33, 1.27, 1.20, 1.18, 1.12, 1.06, 0.64

(6) CMR spectrum (in $CDCl_3$, internal standard: TMS)
δ(ppm): 206.4, 201.5, 192.4, 170.4, 166.6, 157.3, 149.4, 141.4, 136.3, 136.1, 126.3, 125.9, 122.9, 118.2, 100.8, 99.2, 98.5, 96.4, 92.5, 91.5, 84.3, 84.0, 81.2, 77.9, 74.4, 73.0, 69.4, 69.2, 68.2, 67.9, 66.6, 62.1, 54.3, 53.8, 52.8, 51.2, 44.8, 43.2, 41.6, 38.4, 38.0, 35.9, 34.5, 31.5, 31.1, 30.7, 29.6, 26.3, 25.3, 22.0, 21.0, 18.2, 18.0, 17.5, 16.9, 16.1, 15.0, 14.3, 14.0

(7) Specific optical rotation:
$[\alpha]_D^{19} = -55.8°$ (c=1.00, acetone)

(8) Solubility:
DC-11-A-2 is soluble in methanol, ethanol, butanol, acetone, ethyl acetate and chloroform, slightly soluble in benzene and water, and insoluble in petroleum ether and n-hexane.

REFERENCE EXAMPLE 3

In this example, *Micromonospora chalcea* KY 11091 (FERM-P No. 4458, NRRL No. 11,289) is used as a seed strain.

The strain is inoculated into 300 ml of seed medium comprising 4 g/l KCl, 0.5 g/l $MgSO_4.7H_2O$, 1.5 g/l $KH_2PO_4$, 5.0 g/l $(NH_4)_2SO_4$, 20 g/l sucrose, 10 g/l fructose, 10 g/l glucose, 5.0 g/l corn steep liquor and 20 g/l $CaCO_3$ (pH 7.0) in a 2 l-Erlenmeyer flask and cultured at 30° C. with shaking (220 r.p.m.) for 48 hours. The thus obtained seed culture is transferred at a rate of 5% (volume) into a 30 l-jar fermenter containing 15 l of a fermentation medium comprising 60 g/l soluble starch, 10 g/l defatted soybean meal, 10 g/l peptone, 0.5 g/l $K_2HPO_4$, 0.5 g/l $MgSO_4.7H_2O$ and 1 g/l $CaCO_3$. The pH of the medium is adjusted to 7.2 with NaOH before sterilization. Culturing is carried out at 30° C. with aeration and agitation (15 l/min, 250 r.p.m.) for 60 hours without controlling the pH of the medium. The resulting culture liquor is filtered to remove cell bodies and precipitates and to obtain 13 l of filtrate. The filtrate is passed through a column packed with 1 l of non-ionic porous resin (trademark "HP-10", a product of Mitsubishi Chemical Industries) to adsorb the active principles. Then, the resin is washed with water and 30% (V/V) aqueous acetone to remove the impurities. Elution is carried out with acetone and the acetone fractions are concentrated to dryness to obtain a residue which is then dissolved in 30% (V/V) aqueous acetone. The resultant solution is charged on a column packed with 500 ml of active carbon for adsorption and the carbon is washed with 30% (V/V) aqueous acetone. Elution is carried out with acetone, whereby most of the pigments which are present in the solution as impurities is removed. Active fractions are concentrated to dryness and the residue is dissolved in a small amount (about 10 ml) of chloroform containing 2 g/l α-tocopherol. The chloroform solution is gently charged on a column packed with 500 ml of silica gel [trademark: silica gel for chromatography (100-200 mesh), a product of Kanto Kagaku, the same shall apply hereinafter] suspended in advance in chloroform. (Hereinafter, the solvent used in this reference example contains 2 g/l α-tocopherol) Then, the column is thoroughly washed with about 2 l of chloroform. Elution is carried out with a mixed solvent of chloroform and methanol (100:2.5, by volume) to obtain active fractions containing DC-11-B, DC-11, DC-11-A-2 and DC-11-A-3.

From the above fractions, the fractions containing mainly DC-11-B are combined and concentrated, followed by addition of petroleum ether to obtain a powder. The thus obtained powder is dissolved in a small amount of toluene containing 2 g/l α-tocopherol and the solution is charged on a column packed with the same silica gel as above suspended in advance in toluene. Elution is carried out with a mixed solvent of toluene and acetone (2:1, by volume) to obtain the fractions containing DC-11-B. Those fractions are combined and concentrated, followed by addition of petroleum ether to obtain a powder. The powder is washed three times with petroleum ether to remove the α-tocopherol. The thus obtained DC-11-B is purified by silica gel thin layer chromatography using a mixed solvent of ethyl acetate and acetic acid (20:1, by volume) as a developer. Elution is carried out with acetone and the eluate is concentrated to dryness. The residue is dissolved in ethyl acetate and mixed with 0.05 N HCl by shaking. The solvent layer is separated and petroleum ether is added thereto for precipitation, whereby about 20 mg of DC-11-B is obtained as a powder. Physicochemical properties of the thus obtained DC-11-B are as follows:

(1) Melting point: 189°-194° C.
(2) Elementary analysis
H=7.5%; C=61.0%; N=2.2%.
(3) Infrared absorption spectrum
cm$^{-1}$: 3440, 2920, 1760, 1730, 1688, 1632, 1540, 1505, 1448, 1367, 1230, 1119, 1050, 980
(4) PMR spectrum (in CDCl$_3$, internal standard: TMS)
δ(ppm): 9.63, 7.04, 5.8-4.0 (many peaks), 3.76, 3.9-2.2 (many peaks), 2.09, 1.82, 1.63, 1.51, 1.35, 1.29, 1.27, 1.21, 1.18, 1.14, 0.95, 0.65
(5) Specific optical rotation:
$[\alpha]_D^{20} = -92.0°$ (c=1.0, acetone)
(6) Solubility
DC-11-B is soluble in methanol, ethanol, butanol, acetone, chloroform and ethyl acetate, slightly soluble in benzene and water, and insoluble in ethyl ether, petroleum ether and n-hexane.

The following table shows behavior of DC-11-B on thin layer chromatography, which distinguishes DC-11-B from DC-11, DC-11-A-2 and DC-11-A-3.

TABLE

| Developer | Compound | Rf value |
|---|---|---|
| (1) Rf values obtained using silica gel (trademark: DC-Fertigplatten-Kieselgel 60F$_{254}$, E. Merck) | | |
| I. toluene:acetone = 20:30 (by volume, the same shall apply hereinafter) | DC-11 | 0.54 |
| | DC-11-A-2 | 0.47 |
| | DC-11-A-3 | 0.51 |
| | DC-11-B | 0.52 |
| II. ethyl acetate:acetic acid = 20:1 | DC-11 | 0.42 |
| | DC-11-A-2 | 0.47 |
| | DC-11-A-3 | 0.40 |
| | DC-11-B | 0.38 |
| III. chloroform:methanol = 9:1 | DC-11 | 0.57 |
| | DC-11-A-2 | 0.52 |
| | DC-11-A-3 | 0.56 |
| | DC-11-B | 0.53 |
| (2) Rf values obtained using silica gel (trademark: DC-Fertigplatten Kieselgel 60F$_{254}$ Silanisiert, E. Merck) | | |
| chloroform:dioxane = 95:5 | DC-11 | 0.60 |
| | DC-11-A-2 | 0.40 |
| | DC-11-A-3 | 0.57 |
| | DC-11-B | 0.57 |

As is the case with DC-11, DC-11-A-2 and DC-11-A-3, DC-11-B does not show clear parent ion in mass spectroscopic analysis.

However, it seems reasonable that DC-11-B is a compound represented by a molecular formula: $(C_{65-69} H_{94-102} N_2 O_{22-26})_n$ (n=1 or 2) and having the molecular weight: 1254-1374 or 2508-2748 from the results of elementary analysis and NMR, the physicochemical properties of DC-11, DC-11-A-2 and DC-11-A-3, and the fact that DC-11-B can easily be converted to DC-11 by treating with an oxidizing agent.

From the above physicochemical properties, DC-11-B proves to be a novel compound which is different from DC-11, DC-11-A-2 and DC-11-A-3 disclosed in prior applications.

What is claimed is:

1. A composition of matter having an antibacterial activity which is represented by the formula (1)

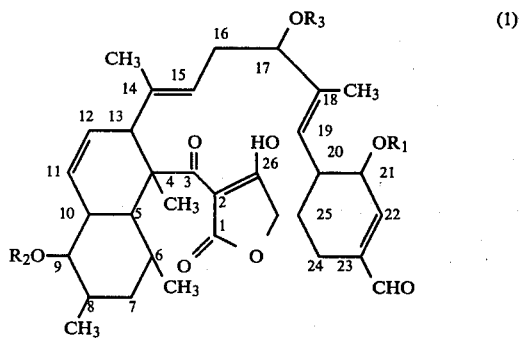

wherein R$_1$ and R$_2$ may be the same or different substituents and represent a hydrogen atom or an acyl group and R$_3$ represents a hydrogen atom, an acyl group or a tetronitrose represented by the formula (2)

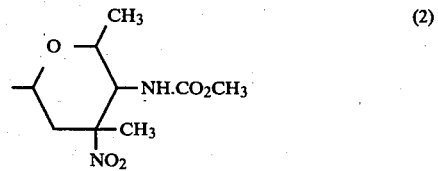

and the pharmaceutically acceptable salts thereof.

2. A pharmaceutical composition for eliciting an antibacterial response comprising a pharmaceutical carrier and, as an active ingredient, an antibacterially effective amount of the composition of matter of claim 1.

* * * * *

UNITED STATES PATENT AND TRADEMARK OFFICE
CERTIFICATE OF CORRECTION

PATENT NO. : 4,393,056

DATED : July 12, 1983

INVENTOR(S) : Fusao Tomita et al.

It is certified that error appears in the above-identified patent and that said Letters Patent is hereby corrected as shown below:

Column 5, line 55, before the table, insert:

--TABLE 1

Rf values obtained using silica gel plate (trademark: DC-Fertigplatten Kieselgel $60F_{254}$, a product of E. Merck) and developer comprising chloroform and methanol (9 : 1 by volume) --

Column 9, line 58, "eluant" should read -- eluate --.

Signed and Sealed this

Twenty-sixth Day of June 1984

[SEAL]

Attest:

GERALD J. MOSSINGHOFF

Attesting Officer   Commissioner of Patents and Trademarks